United States Patent
Wall Warner et al.

(10) Patent No.: US 11,107,032 B2
(45) Date of Patent: *Aug. 31, 2021

(54) METHODS AND SYSTEMS FOR CLOUD-AND MOBILE DEVICE-BASED BIOLOGICAL INVENTORY TRACKING

(71) Applicant: Global Specimen Solutions, Inc., Raleigh, NC (US)

(72) Inventors: Amelia Wall Warner, Raleigh, NC (US); Mark Anthony Collins, Raleigh, NC (US)

(73) Assignee: Global Specimen Solutions, Inc., Raleigh, NC (US)

( * ) Notice: Subject to any disclaimer, the term of this patent is extended or adjusted under 35 U.S.C. 154(b) by 248 days.

This patent is subject to a terminal disclaimer.

(21) Appl. No.: 15/768,138

(22) PCT Filed: Sep. 29, 2016

(86) PCT No.: PCT/US2016/054314
§ 371 (c)(1),
(2) Date: Apr. 13, 2018

(87) PCT Pub. No.: WO2017/058995
PCT Pub. Date: Apr. 6, 2017

(65) Prior Publication Data
US 2018/0300672 A1    Oct. 18, 2018

Related U.S. Application Data

(60) Provisional application No. 62/236,188, filed on Oct. 2, 2015.

(51) Int. Cl.
*G06K 19/00* (2006.01)
*G02B 21/00* (2006.01)
(Continued)

(52) U.S. Cl.
CPC ......... *G06Q 10/087* (2013.01); *G06F 16/381* (2019.01); *G06F 16/50* (2019.01);
(Continued)

(58) Field of Classification Search
CPC ........ G16H 40/67; G16H 40/63; G16H 20/40; G16H 10/60; G16H 10/65; G16H 50/30;
(Continued)

(56) References Cited

U.S. PATENT DOCUMENTS 9,854,111 B2    12/2017    Wall Warner et al.
2003/0105879 A1    6/2003    Olson
(Continued)

FOREIGN PATENT DOCUMENTS

| CN | 102270292 | 12/2011 |
| JP | 2014107748 A | 6/2014 |
| WO | 2017058995 A1 | 4/2017 |

OTHER PUBLICATIONS

EP16852544.2, "Extended European Search Report", dated Apr. 10, 2019, 7 pages.
(Continued)

*Primary Examiner* — Maroun P Kanaan
(74) *Attorney, Agent, or Firm* — Kilpatrick Townsend & Stockton LLP

(57) ABSTRACT

The subject matter described herein includes methods, systems, and computer program products for biological inventory tracking using cloud services and mobile devices. According to one method, information is input from a mobile device about a specimen sample. The information includes an image of the specimen sample captured using the mobile device including an identifying indicia. The information is uploaded and stored in an encrypted format accessible to authorized and verified users. At least one characteristic of the specimen sample is determined based (Continued)

on the information. Tracking and status information, as well as notifications or reminders, regarding the specimen sample are provided in real-time or near real-time to the mobile device.

16 Claims, 3 Drawing Sheets

(51) Int. Cl.
| | | |
|---|---|---|
| *G06Q 10/08* | (2012.01) | |
| *G06F 16/50* | (2019.01) | |
| *G06F 16/38* | (2019.01) | |
| *H04L 29/08* | (2006.01) | |
| *H04L 29/06* | (2006.01) | |
| *G16H 40/20* | (2018.01) | |
| *G16H 40/40* | (2018.01) | |
| *G16H 40/67* | (2018.01) | |
| *G16H 30/20* | (2018.01) | |
| *H04W 12/033* | (2021.01) | |
| *H04N 1/00* | (2006.01) | |
| *G16H 80/00* | (2018.01) | |

(52) U.S. Cl.
CPC ............ *G16H 30/20* (2018.01); *G16H 40/20* (2018.01); *G16H 40/40* (2018.01); *G16H 40/67* (2018.01); *G16H 80/00* (2018.01); *H04L 29/06* (2013.01); *H04L 67/06* (2013.01); *H04L 67/10* (2013.01); *H04L 67/1097* (2013.01); *H04N 1/00307* (2013.01); *H04W 12/033* (2021.01); *H04L 63/0428* (2013.01); *H04N 2201/0084* (2013.01)

(58) Field of Classification Search
CPC ........ G16H 30/20; G16H 40/20; G16H 40/40; G16H 50/70; G16H 10/40; G16H 30/40; G16H 50/20; G16H 15/00; G16H 20/10; G02B 2027/014; G02B 2027/0178; G02B 27/0093; G02B 27/017; G02B 2027/0112; G06F 16/381; G06F 16/50; G06F 1/163; G06F 3/013; G06F 2203/0331; G06F 3/005; G06F 3/011; G06F 3/017; G06F 19/321; G06F 16/51; G06F 3/04845; G06Q 10/087

See application file for complete search history.

(56) References Cited

U.S. PATENT DOCUMENTS

| | | |
|---|---|---|
| 2003/0115481 A1 | 6/2003 | Baird et al. |
| 2004/0117215 A1 | 6/2004 | Marchosky |
| 2011/0126273 A1* | 5/2011 | Bhatia ..................... G06F 21/31 726/7 |
| 2012/0037700 A1 | 2/2012 | Walji et al. |
| 2012/0042164 A1 | 2/2012 | Bernard et al. |
| 2013/0010094 A1* | 1/2013 | Satish ....................... G06T 5/00 348/77 |
| 2013/0154829 A1* | 6/2013 | Mostov .................. G08B 25/10 340/539.13 |
| 2013/0273524 A1 | 10/2013 | Ehrenkranz |
| 2013/0314522 A1 | 11/2013 | Mordchai et al. |
| 2014/0027517 A1 | 1/2014 | Gu |
| 2014/0117080 A1 | 5/2014 | Schwarz et al. |
| 2014/0243650 A1 | 8/2014 | Oren et al. |
| 2015/0054975 A1* | 2/2015 | Emmett ............. H04N 5/23245 348/220.1 |
| 2015/0209114 A1* | 7/2015 | Burkholz ............ G06F 19/3418 600/562 |
| 2016/0171852 A1 | 6/2016 | Lin et al. |
| 2017/0149708 A1 | 5/2017 | Baumgartner |

OTHER PUBLICATIONS

CA3,001,151, "Office Action", dated Feb. 19, 2019, 3 pages.
AU2016332939, "First Examination Report", dated Apr. 27, 2020, 3 pages.
CA3,001,151, "Office Action", dated Mar. 10, 2020, 3 pages.
SG11201802943X, "Notice of Decision to Grant", dated Sep. 17, 2019, 1 page.
CN Application No. 201680068331.6, Office Action, dated Jun. 3, 2020, 17 pages.

* cited by examiner

METHODS AND SYSTEMS FOR CLOUD- AND MOBILE DEVICE-BASED BIOLOGICAL INVENTORY TRACKING

CROSS-REFERENCE TO RELATED APPLICATION

This application is a U.S. national phase of International Application No. PCT/US2016/054314, filed Sep. 29, 2016, and published as International Publication No. WO 2017/058995 A1 on Apr. 6, 2017, which application claims the benefit of priority of U.S. provisional patent application No. 62/236,188 titled "Methods and Systems for Cloud- And Mobile Device-Based Biological Inventory Tracking," filed on Oct. 2, 2015, the contents of all of which is incorporated herein by reference in their entireties.

BACKGROUND

Field of the Invention

The present invention relates to a specimen sample collection mobile application, and more specifically, to methods and systems for biological inventory tracking using cloud services and mobile devices.

DESCRIPTION OF THE RELATED ART

In the field of medicine, where collection of biological inventory such as specimen samples (e.g., blood, urine, etc.) is common, inventory cataloguing is an important function, and convenient and accurate tracking of inventory items is desirable and often necessary to maintain compliance with regulatory guidelines. While some options for digital sample collection and management exist in the marketplace today, most are cumbersome, complex, and take too much time for users to submit data. For example, while many technicians have smartphones and maintain digital schedules for when specimens are to be collected, there is no convenient way to leverage these items to quickly and easily input the relevant details of a specimen once it has been collected, track the status of the specimen throughout testing, or prompt the technician if there is a mismatch between the expected specimen collection schedule and the actual specimen collection records.

Accordingly, a need exists for a convenient solution for sending sample data to other systems such as clinical trial management systems and electronic health records.

BRIEF SUMMARY

The subject matter described herein includes methods, systems, and computer program products for biological inventory tracking using cloud services and mobile devices. According to one method, information is inputted from a mobile device regarding a specimen sample. The information includes an image of the specimen sample captured using the mobile device and an identifying indicia. The information is uploaded and stored in an encrypted format which is accessible to authorized and verified users. At least one characteristic of the specimen sample is determined based on the information. Tracking and status information, as well as notifications or reminders, regarding the specimen sample are provided in real-time or near real-time to the mobile device.

In one embodiment, the system may include an application whose functionality is distributed across multiple platforms: a mobile application running on mobile devices, a cloud-hosted service, and a web-based application. In another embodiment, a system includes a mobile device, a data store, and a wireless communications system configured to perform the method described herein.

DETAILED DESCRIPTION

The subject matter described herein includes an easy-to-use mobile application to assist customers with automating tracking of specimen sample collection. In contrast to conventional configurations, which are cumbersome, complex, and take too much time for users to submit data, the present disclosure leverages a hybrid development framework (such as PhoneGap, Ionic, or Appcelerator) to create an intuitive interface for automating specimen sample collection.

For example, the embodiments disclosed herein use mobile and cloud technology in combination with digital image files to allow a technician to use a mobile device to capture information of a biological specimen sample for cataloging and tracking at point of collection. The invention described herein allows for recoding of images, barcode or other indicator information, location information, and other metadata. A cloud-hosted inventory management system may provide for post-collection tracking, e.g. the specimen sample status, chat or other conversation regarding the specimen sample, packaging information, storage status, and delivery.

Using a portable electronic device, such as a smartphone equipped for digital imaging, a digital image (or images) of the inventory item associated with a pre-printed barcode or other indicator is created. The image and other data is captured in the file by a mobile application executed on the mobile device and then synchronized with a management system over the Internet or other wireless connection or direct data transfer. The cloud-based data store may then automatically create and store the information for every specimen sample, associating the specimen sample image with the barcode detected in the image (if the barcode or other indicator is optically recognizable) as well as with any other data included in the file.

In one embodiment, metadata may be captured along with the captured image. Image metadata may include text information pertaining to an image file that is embedded into the file or contained in a separate file that is associated with it. Image metadata may include details relevant to the image itself as well as information about its production. Some metadata may be generated automatically by the device capturing the image. Additional metadata may be added manually and edited by the technician or an administrator. Metadata may include a GPS location, which can be used to link to a facility from which the sample is being collected.

Figure 1:
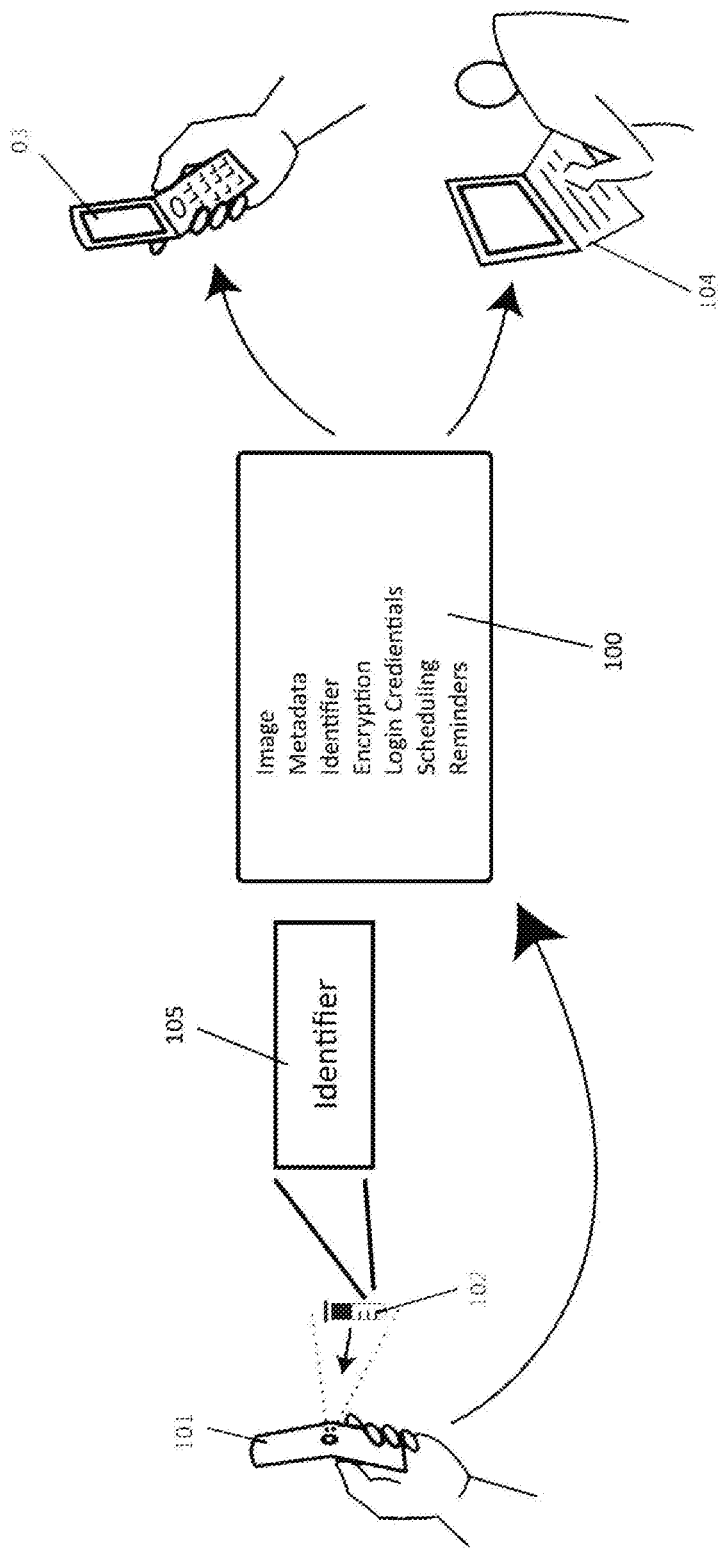
FIG. 1 is an overview diagram illustrating example components and functions for cloud hosted specimen sample tracking using a mobile application according to an embodiment of the subject matter described herein.

FIG. 1 is an overview diagram illustrating example components and functions for cloud hosted specimen sample tracking using a mobile application according to an embodiment of the subject matter described herein. For example, information is input from a mobile device 101 about a specimen sample 102, such as a vial of blood. The mobile application may also request additional information to be input relating to the sample 102, environment, and the like. The additional information may be input by the user of the mobile device. The information includes an image of the specimen sample 102 captured using the mobile device 101 including an identifying indicia 105 (e.g., the identifying indicia may include a barcode label affixed to the blood vial). The information is then uploaded and stored in an offsite server 100 (e.g., at a cloud-hosted service such as Amazon S3, or cloud hosted data service) in an encrypted format accessible to authorized and verified users. Next, at least one characteristic of the specimen sample 102 is determined based on the information (e.g., that the color of the blood is red rather than green). Tracking and status information, as well as notifications or reminders, regarding the specimen sample 102 may be provided in real-time or near real-time to one or more of the computing devices disclosed herein. Each of these steps and aspects will be described in greater detail below.

Referring to FIG. 1, the mobile device 101 may include, for example, a smart phone with an integrated camera. The embodiments herein will be described and illustrated primarily in relation to smart phones, however it is appreciated that portable digital cameras, laptops, tablets, and similar imaging devices, or other electronic devices equipped with camera or imaging technology may be used without departing from the scope of the subject matter described herein. Such electronic devices may thus include any computing and/or communication devices adapted to communicate over fixed or wireless networks, such as smartphones or tablet computers, similarly adapted to have either on-board camera or imaging technology, or alternatively connected to a camera or other imaging device (either by a fixed connection or by a wireless connection, such as Wi-Fi, Bluetooth, or a similar appropriate wireless protocol). It will be appreciated by those skilled in the art, however, that this description is not intended to limit the scope of the described embodiments to implementation on these particular devices. For example, the methods and systems described herein may be applied to any appropriate communication device or data processing device that is suitably adapted, whether portable or wirelessly enabled or not, whether provided with voice communication capabilities or not, and additionally or alternatively adapted to process data and carry out operations on data in response to user commands for any number of purposes, including productivity and entertainment. Thus, the embodiments described herein may be implemented on computing devices adapted for digital imaging or photography, including without limitation cellular phones, smartphones, wireless organizers, personal digital assistants, desktop computers, terminals, laptops, tablets, handheld wireless communication devices, notebook computers, entertainment devices such as MP3 or video players, and the like. Unless expressly stated, an electronic device, camera, or imaging device may include any such device.

A technician may capture an image of a biological inventory item or specimen sample 102, such as a vial of a blood with a barcode or other identifier 105 attached to the sample using a mobile device 101. The captured image may also be associated with metadata such as location, time, and credential information. All of this information is transmitted to an offsite server 100 such as a cloud data service or webserver. In one or more embodiments, no confidential information, including the captured image data, are stored on the mobile device 101. The transmission of the information is encrypted and is also stored in an encrypted form in the offsite server 100. In one embodiment, the captured image is analyzed by a human to determine whether the image is valid and acceptable. For example, the image should be well lit and not skewed or out-of-focus, so that both the identifier 105 on the sample 102 is legible and also that potentially useful information about the sample 102 can be determined. This may include whether the sample 102 is an expected color, consistency, or volume. In another embodiment, the mobile device 101, a program executing on an external server, and/or the cloud-based service may automatically perform image analysis to determine whether the image is acceptable. If not, the technician may be prompted on the mobile device 101 to re-capture an image of the sample 102. Once an acceptable image has been captured, a signal may be transmitted to the mobile device 101 to provide an indication to the technician that the image capture process has been successfully completed.

Once image and other data for a specimen sample 102 has been uploaded to the offsite server 100, additional functionality may be available. For example, time and/or location tracking of the sample may be performed, similar to tracking a package, including real-time or near real-time tracking and status information. Thus, a sample 102 may be location and time-stamped when collected and uploaded to the offsite server 100 and then stamped again when the sample 102 arrives at a central testing facility or laboratory. Additional images of the sample may be captured to further provide an indication of progress or status of the sample 102. For example, an image of the sample 102 captured upon collection may be compared with an image of the same sample 102 captured several days later upon arrival at a laboratory in order to determine any differences and thus infer any potential problems. Example differences which may be determined include a volume of the sample 102, sample quality, or whether the sample container (e.g., vial) is broken or compromised in any way.

After successful transmission of the image, the captured image may be removed from permanent and temporary memory of the mobile device 101, along with all identifying information for security purposes. In one or more embodiments, the mobile device 101 may have control code configured to delete the captured image and data upon receiving a notification that the image has been successfully uploaded and/or accepted.

In one embodiment, an administration interface 104 may be provided to the offsite server 100 in order to manage the stored data. This may allow users other than the technicians collecting the samples and uploading the captured image data to perform additional functions which may not be accessible via the mobile app. For example, the offsite server 100 may integrate with various electronic calendar or scheduling systems to determine when samples are expected to be collected and provide reminders or other prompts to technicians, via the mobile app, in the event that there is a mismatch between the schedule and the received data. In one scenario, a patient is expected to provide a blood sample at 1:00 PM according to a schedule. The patient, however, cancels the appointment and the sample is never collected. After a predetermined time has elapsed after the appointment time, the mobile application may alert or notify the technician that an expected 1:00 PM sample from that patient was not received. If, however, the technician updates the calendar before 1:00 PM to show the cancellation, the mobile application may avoid notifying the technician (e.g., there is no longer a mismatch). In another scenario, the patient is expected to provide a sample at 1:00 PM does arrive and provides a sample, but the technician forgets to capture an image of the sample and upload it. In such case, the mobile application may alert or notify the technician that an expected 1:00 PM sample from that patient was not received. The technician may then provide the sample data.

In one or more embodiments, a program residing on the mobile device 101 or on an external server may de-identify any portion of or any image containing sensitive information or information not expected from a specimen sample 102. For example, the program may be configured to identify a human and then blur or other render non-viewable the human in the image. Additionally, the program may be configured to identify documents in the background of an image that contain sensitive information and perform similar image processing on those documents.

Figure 2:
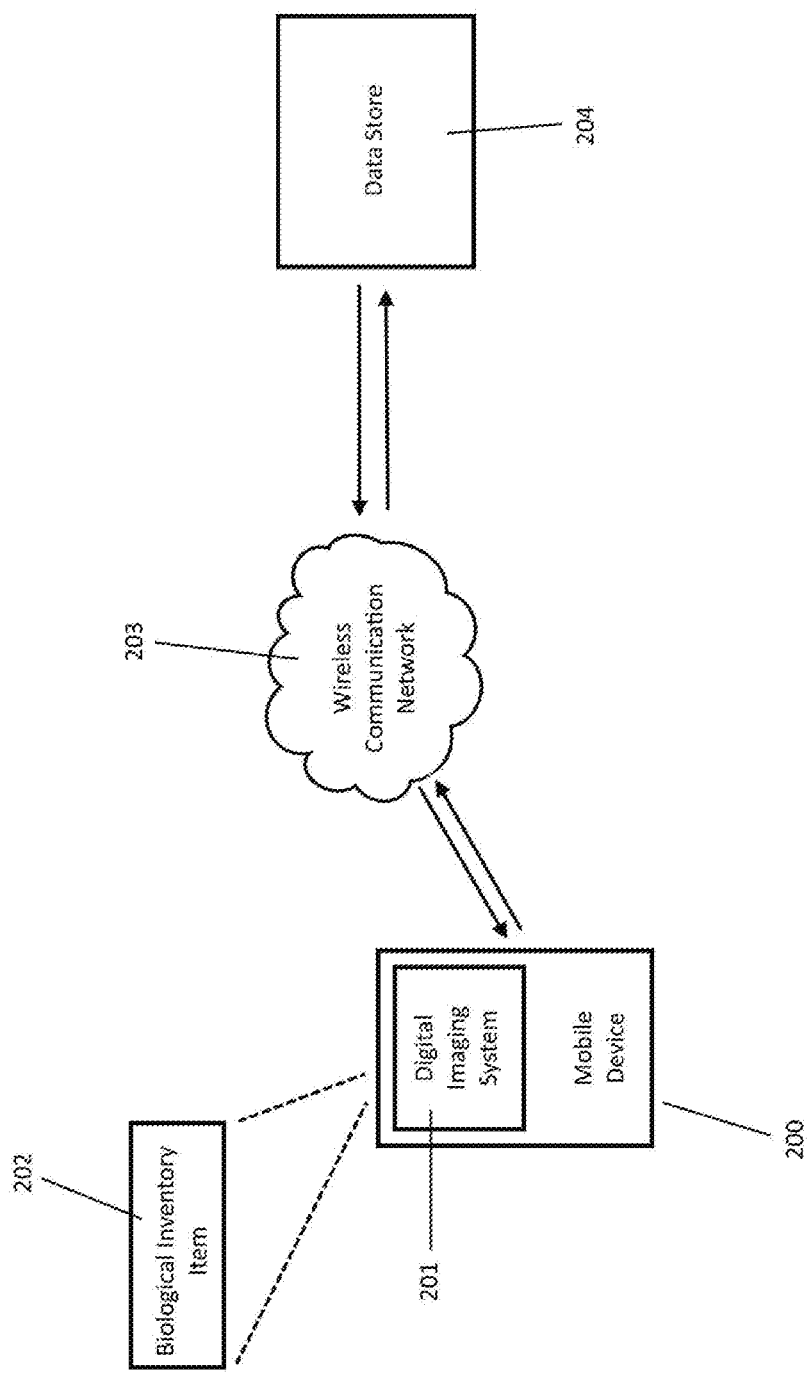
FIG. 2 is a block diagram illustrating an exemplary system for cloud hosted specimen sample tracking using a mobile application according to an embodiment of the invention.

Referring now to FIG. 2, according to one embodiment of the invention, a system for cloud hosted specimen sample tracking using a mobile application is provided. The system may include a mobile device 200 with a digital imaging subsystem 201 configured to receive image data and indicator information for a captured image associated with a biological inventory item 202. The mobile device 200 may be further configured to determine at least one physically attribute of the biological inventory item 202 based on the image data and indicator information. The system may also include a data store 204 configured to receive and store image data and indicator information for the biological inventory item 202 and a wireless communication network 203 for communicating the image data and indicator information for the biological inventory item 202 between the mobile device 200 and data store 204.

Figure 3:
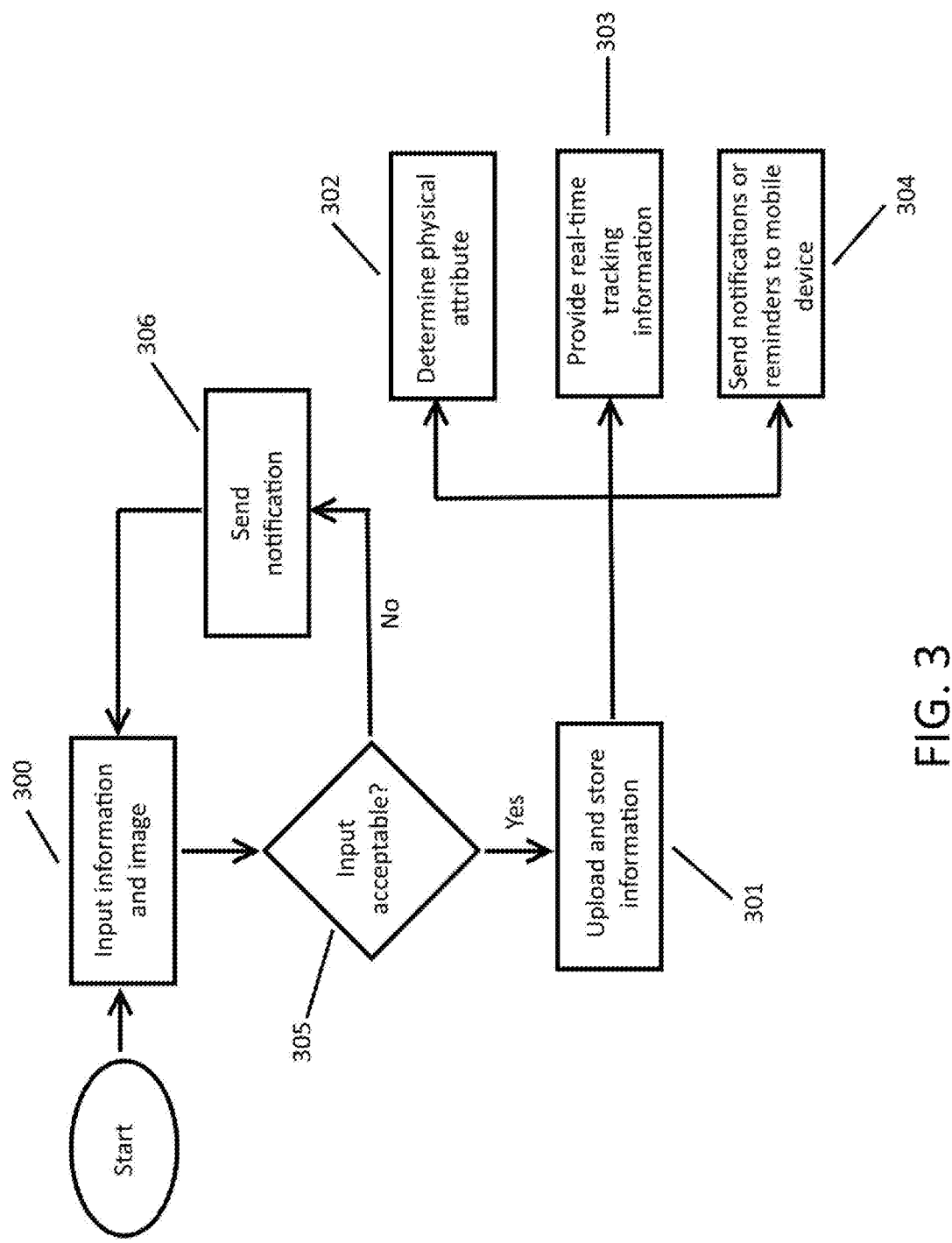
FIG. 3 is a flow chart illustrating an exemplary process for cloud hosted specimen sample tracking using a mobile application according to an embodiment of the invention.

Referring now to FIG. 3, according to another embodiment of the invention, a process for cloud hosted specimen sample tracking using a mobile application is provided. The process may include inputting information from a mobile device about a specimen sample, wherein inputting the information includes capturing an image of the specimen sample using the mobile device and wherein the captured image includes an identifying indicia. The process may further include uploading and storing the information in an encrypted format accessible to authorized and verified users. According to this embodiment of the invention, at least one physical attribute of the specimen sample may be determined based on the information, tracking and status updates may be provided in real-time or near real-time for the specimen sample, and first notification or reminders regarding the specimen sample may be provided to the mobile device.

According to another aspect, the present invention may be useful in contexts in addition to routine clinical practice. For example, the present invention may provide a clear chain of custody for rape kits or other specimens collected in hospitals. Moreover, blood samples or other specimens collected by law enforcement or crime-scene investigators may be uploaded and tracked using the method and systems described herein.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter situation scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in FIG. 1 illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    receiving information from a mobile device about a specimen sample, wherein the information includes a specimen sample image captured using the mobile device and wherein the specimen sample image includes an identifying indicia;
    storing the information in an encrypted format accessible to authorized and verified users;
    receiving an additional image of the specimen sample captured at a testing facility or laboratory;
    comparing, using a processor performing image analysis, the specimen sample image and the additional image to detect changes in the specimen sample with respect to at least one of a change in sample volume, a change in sample quality, a compromised sample container, or a broken sample container;
    determining, using the processor and based on the comparing, any differences between the specimen sample image and the additional image;
    updating at least one of tracking or status information in real-time or near real-time for the specimen sample, wherein the tracking or status information includes an indication with respect to the differences between the specimen sample image and the additional image; and
    sending notifications regarding the specimen sample to the mobile device.

2. The method of claim 1, wherein the notifications include a notification that the specimen sample image is acceptable or not acceptable, and when not acceptable, the method further includes directing the mobile device or a user of the mobile device to capture a subsequent image.

3. The method of claim 1, wherein the notifications include a notification that the specimen sample image that was expected has not been received, wherein an external entity monitors an expected schedule of images to be uploaded.

4. The method of claim 1, further including removing the specimen sample image from the mobile device upon receipt of the specimen sample image by an external server.

5. A computer program product, said computer program product comprising:
    a non-transitory computer readable storage medium having computer readable program code that is executable by a processor for causing the processor to:
    provide information about a specimen sample, wherein the information includes a specimen sample image of the specimen sample captured using a mobile device and wherein the specimen sample image includes an identifying indicia;

upload the information in an encrypted format accessible to authorized and verified users; and receive and display tracking and status notifications in real-time or near real-time for the specimen sample, wherein the tracking and status notifications include an indication with respect to differences between the specimen sample image and an additional image captured at a testing facility or laboratory as determined by image analysis to detect change in the specimen sample with respect to at least one of a change in sample volume, a change in sample quality, a compromised sample container, or a broken sample container.

6. The computer program product of claim 5, wherein the computer readable program code is further executable for receiving a notification that the specimen sample image is acceptable or not acceptable, and when not acceptable, directing a user of the mobile device to capture a subsequent image.

7. The computer program product of claim 5, wherein the computer readable program code is further executable for receiving a notification that the specimen sample image that was expected has not been received, wherein an external entity monitors an expected schedule of images to be uploaded.

8. The computer program product of claim 5, wherein the computer readable program code is further executable for removing the specimen sample image from the mobile device upon receipt by an external server.

9. A server having a processor and a memory, the server configured for:

receiving input information from a mobile device about a specimen sample, wherein the input information includes a specimen sample image captured using the mobile device and wherein the specimen sample image includes an identifying indicia;

storing the input information in the memory in an encrypted format accessible to authorized and verified users;

determining at least one physical attribute of the specimen sample based on the input information;

receiving an additional image of the specimen sample captured at a testing facility or laboratory;

comparing, using the processor and image analysis, the specimen sample image and the additional image to detect changes in the specimen sample with respect to at least one of a change in sample volume, a change in sample quality, a compromised sample container, or a broken sample container;

determining, using the processor and based on the comparing, any differences between the specimen sample image and the additional image;

updating tracking and status information in real-time or near real-time for the specimen sample, wherein the tracking and status information includes an indication with respect to the differences between the specimen sample image and the additional image; and sending notifications regarding the specimen sample to the mobile device.

10. The server of claim 9, wherein the notifications include a notification that the specimen sample image is acceptable or not acceptable, and further configured for, when not acceptable, directing the mobile device or a user of the mobile device to capture a subsequent image.

11. The server of claim 9, further configured for determining that the specimen sample image that was expected has not been received, and generating a notification that the specimen sample image that was expected has not been received.

12. The server of claim 9, further configured for directing the mobile device to remove the specimen sample image therefrom after a successful transmission.

13. The server of claim 9, further configured for identifying confidential, private, or other sensitive information, and further configured for applying an image processing technique to a portion of the specimen sample image having the confidential, private, or sensitive information to render that portion undiscernible.

14. A mobile device comprising:

a processor; and a non-transitory computer readable storage medium having computer readable program code that is executable by the processor for causing the processor to:

provide information about a specimen sample, wherein the information includes a specimen sample image of the specimen sample captured using the mobile device and wherein the specimen sample image includes an identifying indicia;

upload the information in an encrypted format accessible to authorized and verified users; and receive and display tracking and status notifications in real-time or near real-time for the specimen sample, wherein the tracking and status notifications include an indication with respect to differences between the specimen sample image and an additional image captured at a testing facility or laboratory as determined by image analysis to detect change in the specimen sample with respect to at least one of a change in sample volume, a change in sample quality, a compromised sample container, or a broken sample container.

15. The mobile device of claim 14, wherein the computer readable program code is further executable for receiving a notification that the specimen sample image is acceptable or not acceptable, and when not acceptable, directing a user of the mobile device to capture a subsequent image.

16. The mobile device of claim 14, wherein the computer readable program code is further executable for removing the specimen sample image from the mobile device upon receipt by an external server.

* * * * *